United States Patent
Eberly et al.

(10) Patent No.: US 9,970,013 B2
(45) Date of Patent: May 15, 2018

(54) RAPID IN SITU TESTING FOR ENVIRONMENTAL CONTAMINATION

(71) Applicants: Jed O. Eberly, Vicksburg, MS (US); Fiona Crocker, Clinton, MS (US); Karl J. Indest, Ridgeland, MS (US)

(72) Inventors: Jed O. Eberly, Vicksburg, MS (US); Fiona Crocker, Clinton, MS (US); Karl J. Indest, Ridgeland, MS (US)

(73) Assignee: The United States of America as Represented by The Secretary of The Army, Alexandria, VA (US)

( * ) Notice: Subject to any disclaimer, the term of this patent is extended or adjusted under 35 U.S.C. 154(b) by 0 days. days.

(21) Appl. No.: 14/729,732

(22) Filed: Jun. 3, 2015

(65) Prior Publication Data
US 2017/0107515 A1    Apr. 20, 2017

(51) Int. Cl.
| | |
|---|---|
| *C12N 15/115* | (2010.01) |
| *C12N 15/10* | (2006.01) |
| *G01N 27/327* | (2006.01) |
| *G01N 27/30* | (2006.01) |
| *G01N 27/49* | (2006.01) |

(52) U.S. Cl.
CPC ........ *C12N 15/115* (2013.01); *C12N 15/1048* (2013.01); *G01N 27/301* (2013.01); *G01N 27/3277* (2013.01); *G01N 27/49* (2013.01); *C12N 2310/16* (2013.01); *C12N 2320/13* (2013.01)

(58) Field of Classification Search
None
See application file for complete search history.

(56) References Cited

U.S. PATENT DOCUMENTS

| | | | | |
|---|---|---|---|---|
| 2007/0020641 A1* | 1/2007 | Heeger | .................. | B82Y 15/00 435/6.19 |
| 2008/0311677 A1* | 12/2008 | Chin | ................ | G01N 33/54326 436/526 |

* cited by examiner

*Primary Examiner* — Richard A Schnizer
(74) *Attorney, Agent, or Firm* — Brian C. Jones

(57) ABSTRACT

The present invention provides synthetic RNA aptamers that bind RDX. In various embodiments, the synthetic RNA aptamers may include one or more aptamers selected from the group consisting of SEQ ID 1-12. The synthetic RNA aptamers that bind RDX provide an inexpensive, in situ method for testing for RDX, which may be used for both soil and water samples.

13 Claims, 4 Drawing Sheets

SEQUENCE LISTING

```
<160> NUMBER OF SEQ ID NOS: 12

<210> SEQ ID NO 1
<211> LENGTH: 76
<212> TYPE: RNA
<213> ORGANISM: Artificial sequence
<220> FEATURE:
<223> OTHER INFORMATION: Synthetic

<400> SEQUENCE: 1
uagggaagag aaggacauau gaucggacga ggagcaauug agauaugcgc aaauugacua        60
guacaugacc acuuga                                                       76

<210> SEQ ID NO 2
<211> LENGTH: 76
<212> TYPE: RNA
<213> ORGANISM: Artificial sequence
<220> FEATURE:
<223> OTHER INFORMATION: Synthetic

<400> SEQUENCE: 2
uagggaagag aaggacauau gauugacuag uacaugacca cugaaagggc gaauugacua        60
guacaugacc acuuga                                                       76

<210> SEQ ID NO 3
<211> LENGTH: 76
<212> TYPE: RNA
<213> ORGANISM: Artificial sequence
<220> FEATURE:
<223> OTHER INFORMATION: Synthetic

<400> SEQUENCE: 3
uagggaagag aaggacauau gauagcccca gugugcggca aaugggaca auguugacua         60 guacaugacc acuuga                                                       76

<210> SEQ ID NO 4
<211> LENGTH: 76
<212> TYPE: RNA
<213> ORGANISM: Artificial sequence
<220> FEATURE:
```

<223> OTHER INFORMATION: Synthetic

<400> SEQUENCE: 4
uagggaagag aaggacauau gaucacuuga cuaguacaug accacugaaa ggguugacua    60
guacaugacc acuuga    76

<210> SEQ ID NO 5
<211> LENGTH: 75
<212> TYPE: RNA
<213> ORGANISM: Artificial sequence
<220> FEATURE:
<223> OTHER INFORMATION: Synthetic

<400> SEQUENCE: 5
uagggaagag aaggacauau gaucacuuga uugacuagua caugacccuu gauugacuag    60
uacaugacca cuuga    75

<210> SEQ ID NO 6
<211> LENGTH: 76
<212> TYPE: RNA
<213> ORGANISM: Artificial sequence
<220> FEATURE:
<223> OTHER INFORMATION: Synthetic

<400> SEQUENCE: 6
uagggaagag aaggacauau gauaugauga caccguugac auccgguca auuugacua    60 guacaugacc acuuga    76

<210> SEQ ID NO 7
<211> LENGTH: 75
<212> TYPE: RNA
<213> ORGANISM: Artificial sequence
<220> FEATURE:
<223> OTHER INFORMATION: Synthetic

<400> SEQUENCE: 7
uagggaagag aaggacauau gaucacuuga acugaugacu aguacauacc acugacuag    60 uacaugacca cuuga    75

<210> SEQ ID NO 8
<211> LENGTH: 76
<212> TYPE: RNA
<213> ORGANISM: Artificial sequence
<220> FEATURE:
<223> OTHER INFORMATION: Synthetic

<400> SEQUENCE: 8
uagggaagag aaggacauau gauaucguua uccggucgcg gucgaggccc ugcuugacua    60
guacaugacc acuuga    76

<210> SEQ ID NO 9
<211> LENGTH: 76
<212> TYPE: RNA
<213> ORGANISM: Artificial sequence
<220> FEATURE:
<223> OTHER INFORMATION: Synthetic

<400> SEQUENCE: 9
uagggaagag aaggacauau gauggguaug cacacaucag cgacaacugg ccguugacua    60
guacaugacc acuuga    76

```
<210> SEQ ID NO 10
<211> LENGTH: 76
<212> TYPE: RNA
<213> ORGANISM: Artificial sequence
<220> FEATURE:
<223> OTHER INFORMATION: Synthetic

<400> SEQUENCE: 10
uagggaagag aaggacauau gauccggauc cggaaggcaa ucccuccgcg agguugacua      60
guacaugacc acuuga                                                     76

<210> SEQ ID NO 11
<211> LENGTH: 75
<212> TYPE: RNA
<213> ORGANISM: Artificial sequence
<220> FEATURE:
<223> OTHER INFORMATION: Synthetic

<400> SEQUENCE: 11
uagggaagag aaggacauau gaucccacu ccuauuauca uucgugcca gguugacuag        60 uacaugacca cuuga                                                      75

<210> SEQ ID NO 12
<211> LENGTH: 76
<212> TYPE: RNA
<213> ORGANISM: Artificial sequence
<220> FEATURE:
<223> OTHER INFORMATION: Synthetic

<400> SEQUENCE: 12
uagggaagag aaggacauau gaugcaguca acuguacggg guuagucuug cgguugacua     60
guacaugacc acuuga                                                     76
```

RAPID IN SITU TESTING FOR ENVIRONMENTAL CONTAMINATION

STATEMENT REGARDING FEDERALLY SPONSORED RESEARCH OR DEVELOPMENT

The invention described herein was made by an employee of the United States Government and may be manufactured and used by the Government of the United States of America for governmental purposes without the payment of any royalties thereon or therefore.

INCORPORATION OF SEQUENCE LISTING

Incorporated by reference in its entirety herein is a computer-readable nucleotide/amino acid sequence listing submitted concurrently herewith and identified as follows: One 3,311 Byte ASCII (Text) file named "COE-686_SeqList.txt," created on Oct. 5, 2017.

BACKGROUND OF THE INVENTION

1. Field of Invention

This invention relates to the field of chemistry and more specifically to testing for RDX with a ligand-binding assay.

2. Description of Related Art

Since World War II, an explosive known as C-4 has been widely used for military and civilian operations, such as excavation and demolition. C-4 contains an environmental contaminant known 1,3,5-Trinitroperhydro-1,3,5-triazine (RDX). RDX can migrate through soil and contaminate underlying groundwater aquifers and may be harmful to humans at relatively low levels. The EPA has established a lifetime health advisory guidance level of 0.002 milligrams per liter (mg/L) for RDX in drinking water. The EPA has identified more than thirty RDX contaminated sites on its list of national clean-up priorities.

There are several problems known in the art for testing for the presence of RDX to make determinations relevant to a potential need for remediation. RDX concentrations are discrete particles that are irregularly dispersed throughout the soil. The concentration of samples from adjacent areas may vary considerably. Current RDX testing methods are intended to provide data about precise quantities of RDX using highly sensitive, off-site instrumentation to separately test each sample. This type of high-sensitivity off-site testing is not appropriate for wide scale EPA and private environmental remediation projects, and often does not yield the necessary type of data for evaluating dispersal patterns over potentially contaminated site.

For purposes of planning and remediation, it is important to be able to test many samples to determine the presence or absence of contaminants over a dispersed area and patterns of dispersal. Current high-sensitivity testing methods performed off-site are costly and prone to delay because they cannot be performed in situ.

BRIEF SUMMARY OF THE INVENTION

This invention provides synthetic RNA aptamer(s) that bind 1,3,5-Trinitroperhydro-1,3,5-triazine (RDX).

This invention also provides a method for detecting RDX involving the steps of admixing a buffered solution of a synthetic RNA aptamer that binds RDX with a sample in need of testing for RDX, and assaying the sample for RDX.

This invention also provides a biosensor apparatus for RDX. The apparatus for RDX is made of a plurality of synthetic RNA aptamers that bind RDX. The synthetic RNA aptamers are modified to link to an electrode. The surface electrode is linked to the plurality of synthetic RNA aptamers.

BRIEF DESCRIPTION OF SEVERAL VIEWS OF THE DRAWING(S)

TERMS OF ART

As used herein, the term "assay" is a test or testing for the quantity, presence or absence of a substance.

As used herein, the term "synthetic RNA" refers to a RNA molecule that does not occur naturally.

As used herein, the term "synthetic RNA aptamer" refers to a RNA molecule that includes nucleotides having the chemical structure that binds a substance.

DETAILED DESCRIPTION OF THE INVENTION

Figure 1:
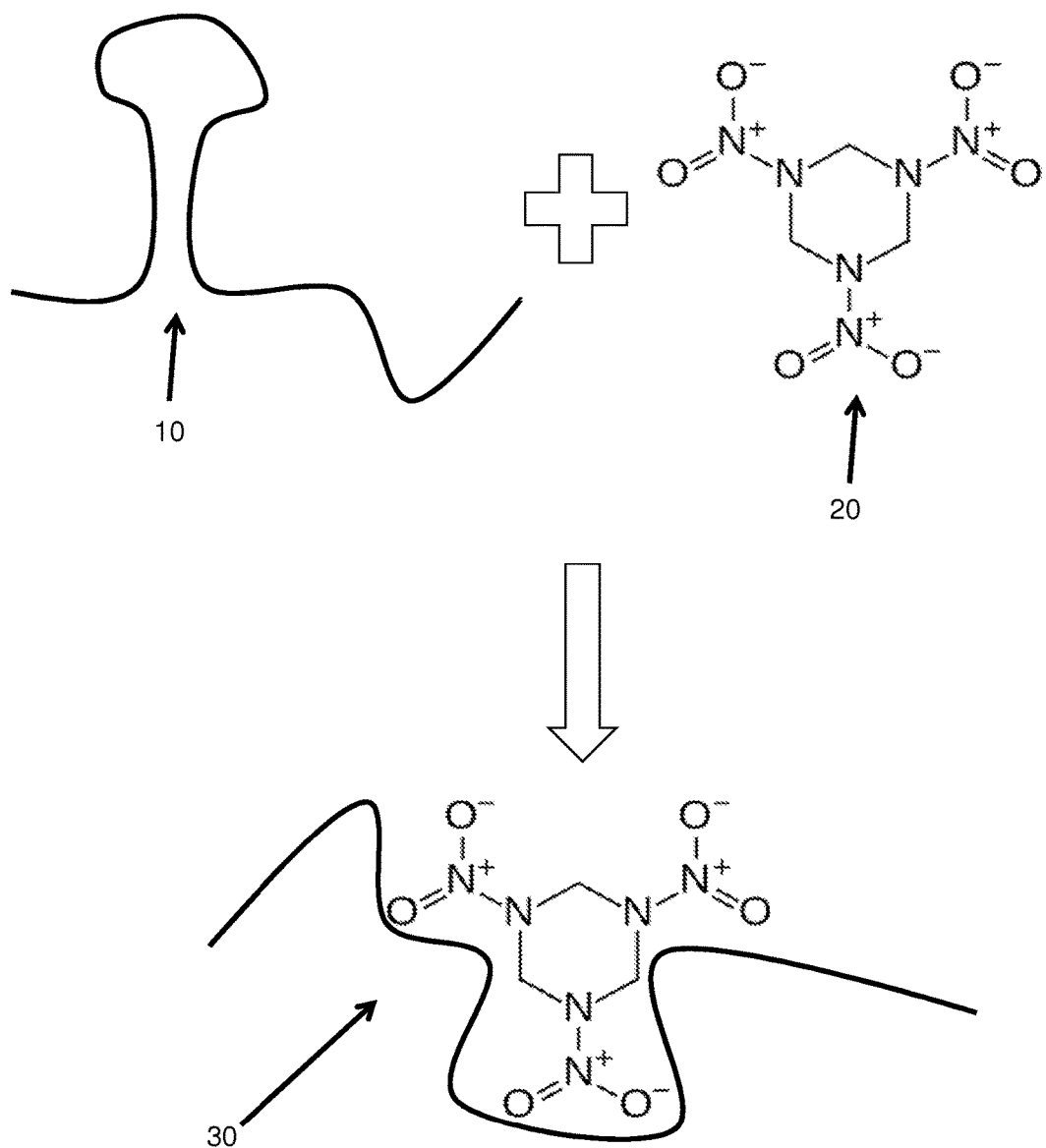
FIG. 1 is a schematic illustrating an exemplary embodiment of how a synthetic RNA aptamer binds to RDX.

FIG. 1 is a schematic illustrating how an exemplary embodiment of a synthetic RNA aptamer 10 binds to RDX 20. In this exemplary embodiment, synthetic RNA aptamer 10 binds to RDX 20 by the formation of secondary structures. The combination of synthetic RNA aptamer 10 secondary structures and three-dimensional tertiary structures enables synthetic RNA aptamer 10 to bind target RDX 20. The combination of synthetic RNA aptamer 10 and RDX 20 forms a binding complex 30.

In the exemplary embodiment, synthetic RNA aptamer 10 is a 76 base-pair synthetic RNA aptamer including a thirty base pair binding region flanked by T7 primer binding sites. In the exemplary embodiment shown, the use of T7 primer binding sites simplifies the amplification steps during systematic evolution of ligands by exponential enrichment (SELEX) and sequencing. However, in alternate embodiments, other primer binding sequences may be used. The exemplary synthetic RNA aptamer 10 illustrated is developed by preparing a library of synthetic RNA sequences containing a thirty nucleotide variable region. This library was then subjected to multiple rounds of SELEX, to enrich for sequences that bind RDX 20.

Table 1 illustrates specific synthetic aptamer sequences capable of binding RDX 20. The RNA sequence of the twelve synthetic aptamers form structures that have binding characteristics that allow them to bind to RDX 20. It should be noted that the sequence of synthetic RNA aptamer(s) 10 can be modified by one skilled in the art to change, delete or add nucleotides to obtain synthetic RNA aptamer(s) 10 that form structures that have binding characteristics that allow synthetic RNA aptamer(s) 10 to bind to RDX 20. For example, the synthetic RNA aptamers 10 shown in Table 1 differ in as much as 50 percent homology, but still have the desired binding characteristics that allow them to bind to RDX 20 and to form binding complex 30.

TABLE 1

Sequences of RDX binding synthetic RNA aptamers

| Clone | Sequence |
|---|---|
| 1 | UAGGGAAGAGAAGGACAUAUGAUCGGACGAGGAGCAAUUGA GAUAUGCGCAAAUUGACUAGUACAUGACCACUUGA SEQ ID NO. 1 |
| 2 | UAGGGAAGAGAAGGACAUAUGAUUGACUAGUACAUGACCAC UGAAAGGGCGAAUUGACUAGUACAUGACCACUUGA SEQ ID NO. 2 |
| 3 | UAGGGAAGAGAAGGACAUAUGAUAGCCCCAGUGUGCGGCAA AUGGGACAAUGUUGACUAGUACAUGACCACUUGA SEQ ID NO. 3 |
| 4 | UAGGGAAGAGAAGGACAUAUGAUCACUUGACUAGUACAUGA CCACUGAAAGGGUUGACUAGUACAUGACCACUUGA SEQ ID NO. 4 |
| 5 | UAGGGAAGAGAAGGACAUAUGAUCACUUGAUUGACUAGUAC AUGACCCUUGAUUGACUAGUACAUGACCACUUGA SEQ ID NO. 5 |
| 6 | UAGGGAAGAGAAGGACAUAUGAUAUGAUGACACCGUUGACA UCCGGGUCAAUUUUGACUAGUACAUGACCACUUGA SEQ ID NO. 6 |
| 7 | UAGGGAAGAGAAGGACAUAUGAUCACUUGAACUGAUGACUA GUACAUACCACUUGACUAGUACAUGACCACUUGA SEQ ID NO. 7 |
| 8 | UAGGGAAGAGAAGGACAUAUGAUAUCGUUAUCCGGUCGCGG UCGAGGCCCUGCUUGACUAGUACAUGACCACUUGA SEQ ID NO. 8 |
| 9 | UAGGGAAGAGAAGGACAUAUGAUGGGUAUGCACACAUCAGC GACAACUGGCCGUUGACUAGUACAUGACCACUUGA SEQ ID NO. 9 |
| 10 | UAGGGAAGAGAAGGACAUAUGAUCCGGAUCCGGAAGGCAAU CCCUCCGCGAGGUUGACUAGUACAUGACCACUUGA SEQ ID NO. 10 |
| 11 | UAGGGAAGAGAAGGACAUAUGAUCCCCACUCCUAUUAUCAU UCUGUGCCAGGUUGACUAGUACAUGACCACUUGA SEQ ID NO. 11 |
| 12 | UAGGGAAGAGAAGGACAUAUGAUGCAGUCAACUGUACGGGG UUAGUCUUGCGGUUGACUAGUACAUGACCACUUGA SEQ ID NO. 12 |

One skilled in the art can prepare RNA oligonucleotides shown in Table 1 by enzymatic transcription or automated solid-phase synthesis. Enzymatic synthesis can produce relatively long transcripts in significant quantities, while commercial non-enzymatic RNA chemical synthesis can produce RNAs that are 40-80 nucleotides in length. Industrial scale production of RNA may by chemical synthesis, by fermentation or by any other method known in the art for producing synthetic RNA.

Synthetic RNA aptamers 10 shown in Table 1 can be used to detect RDX 20 in soil and water samples. The sample tested for RDX 20 can include soil or water. Synthetic RNA aptamers 10 shown in Table 1 have binding characteristics that allow them to bind to RDX 20. These binding characteristics include high affinity and specificity for RDX 20. Affinity refers to the tendency of a ligand molecule to bind to a biological molecule.

Figure 2:
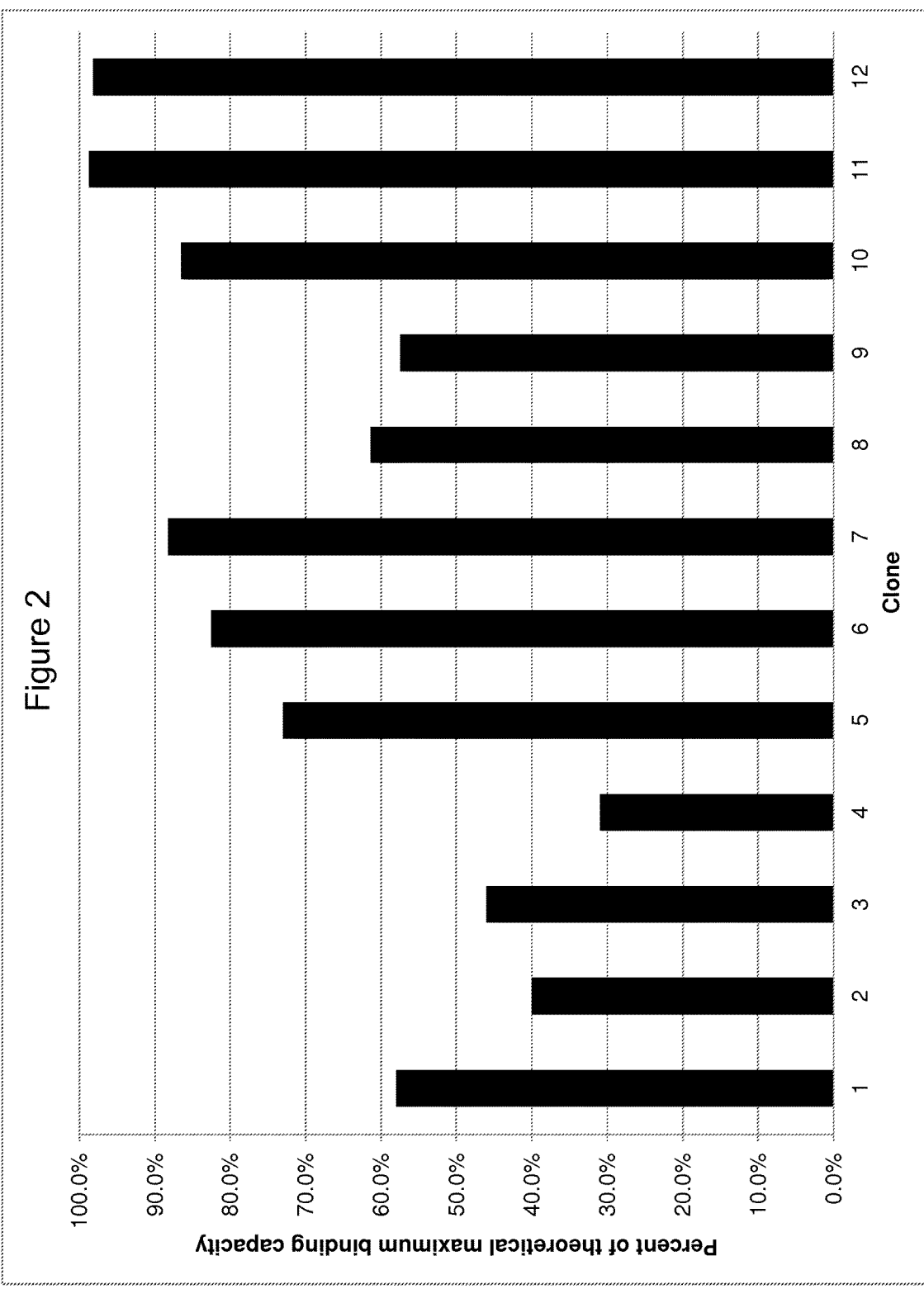
FIG. 2 is a graph illustrating the binding affinity of various embodiments of synthetic RNA aptamers for testing the presence of RDX.

FIG. 2 is a graph illustrating the binding affinity of various embodiments of synthetic RNA aptamers 10 for testing the presence of RDX 20. Synthetic RDX aptamers 10 display high affinity for RDX 20 with several clones capable of achieving almost 100% of the theoretical binding capacity.

FIG. 2 assumes that there is a 1:1 molar ratio between the aptamer and target and that one aptamer will bind one molecule of RDX 20. In the exemplary embodiment shown, the percent of theoretical binding capacity ranges from approximately 30 to approximately 100 percent. In other embodiments, the percent of theoretical binding capacity ranges from approximately 80 to approximately 100 percent.

Table 2 shows the percent of theoretical maximum binding capacity for each clone.

| Clone | Percent of theoretical maximum binding capacity |
|---|---|
| 1 | 58.0% |
| 2 | 40.0% |
| 3 | 46.0% |
| 4 | 31.0% |
| 5 | 73.0% |
| 6 | 82.5% |
| 7 | 88.3% |
| 8 | 61.4% |
| 9 | 57.5% |
| 10 | 86.6% |
| 11 | 98.7% |
| 12 | 98.2% |

Deriving the data in FIG. 2 required testing the binding affinity of synthetic RNA aptamers 10 using the following exemplary method. The method dissolved two and a half micrograms of the synthetic RNA aptamer(s) 10 in 100 uL of a binding buffer consisting of 100 mM sodium chloride (NaCl), 5 mM magnesium chloride (MgCl2), and 25 mM Tris-HCl, pH 6. An aliquot of RDX 20 was dried down and resuspended in the aptamer-buffer solution at final concentrations ranging from 1-100 ppm and allowed to react for 1 hour at room temperature with constant stirring. Centrifugation removed synthetic RDX aptamers 10 with bound RDX 20 from solution by and HPLC measured RDX 20 remaining in solution.

One skilled in the art may use alternative methods to measure bound or unbound RDX 20. For example, in alternative embodiment, the assay can be an electrochemical assay platform. In another embodiment, synthetic RNA aptamer 10 is modified to covalently link to a detectable label and the detectable label is covalently linked to synthetic RNA aptamer 10.

Figure 3:
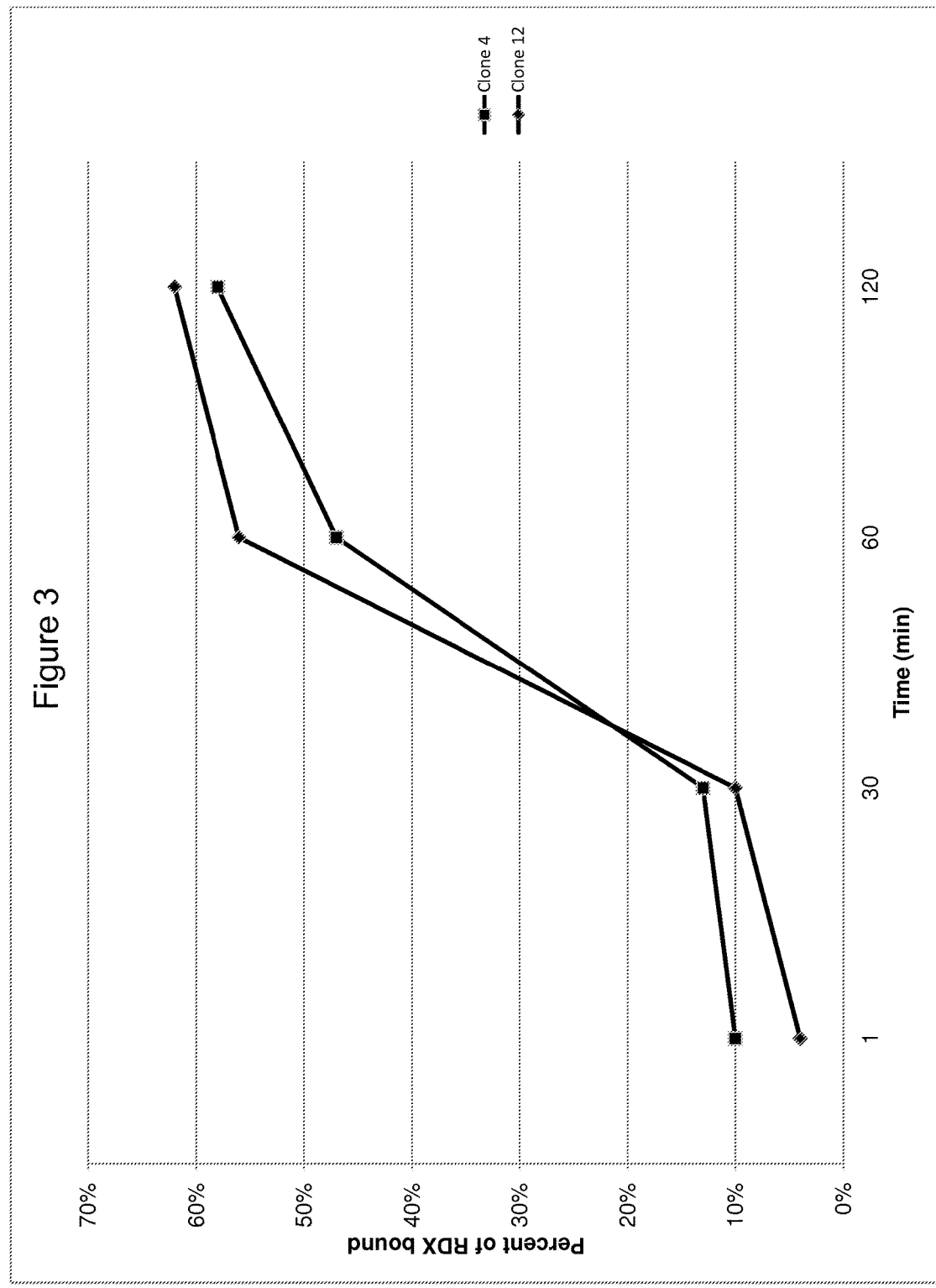
FIG. 3 is a graph illustrating the percent of total RDX bound by synthetic RNA aptamers as a function of time for clones 4 and 12.

FIG. 3 is a graph illustrating the percent of total RDX 20 bound by synthetic RNA aptamers 10 as a function of time for clones 4 and 12. The exemplary synthetic RNA aptamers 10 illustrate a range of binding times. Even lower affinity synthetic RNA aptamers 10 demonstrate a fast response time, binding over 50% of available RDX 20 in one hour. The specificity in this context refers to the ability of synthetic RNA aptamers 10 to bind to the desired target and not bind similar compounds. Synthetic RNA aptamers 10 showed no affinity to 2-4-dinitroanisole (DNAN) and trinitrotoluene (TNT), which are structurally similar compounds used in explosive compositions.

Figure 4:
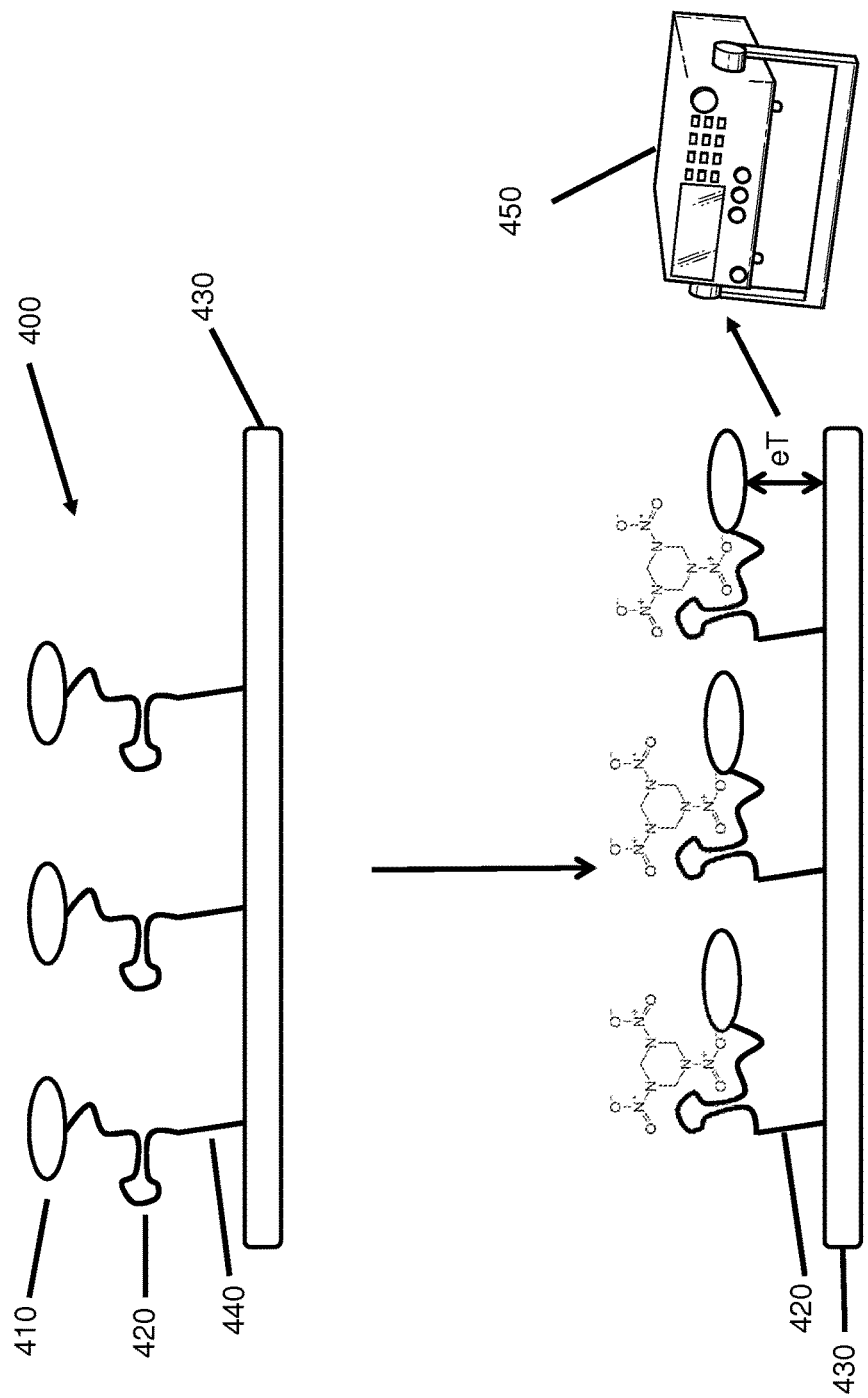
FIG. 4 is a schematic of an exemplary embodiment of a synthetic RNA aptamer electrical-chemical signal transducer.

FIG. 4 is a schematic of an exemplary embodiment of a synthetic RNA aptamer electrical-chemical signal transducer 400. Transducer 400 includes a redox probe 410, a biosensor 420 and an electrode 430. In the exemplary embodiment shown, biosensor 420 is made of a bio-recognition layer including a plurality of synthetic RNA aptamers 10 that bind RDX 20. Synthetic RNA aptamers 10, in this exemplary embodiment, are modified with a 5' C6 disulfide linker 440 for covalent attachment to the surface of electrode 430. In the exemplary embodiment shown, synthetic RNA aptamers 10 also have a 3'-amino modification to covalently attach redox probe 410, such as for example ferrocene (Fc).

In the exemplary embodiment shown, the addition of RDX 20 causes a conformational change in synthetic RNA aptamers 10, which changes the distance between redox probe 410 and a surface of electrode 430, which in turn changes the efficiency of electron transfer (eT). A potentiostat 450 measures the change in current over a voltage gradient. The amplitude of the current corresponds to the concentration of RDX 20. Potentiostat 450 is an electronic instrument that controls the voltage difference between a working electrode and a reference electrode.

A biological sensor can detect the existence of the target molecule within a relatively short time period. Biosensors are hybrid analytical devices that amplify signals generated from the specific interaction between a receptor, such as a binding region, and a ligand of interest, through a biophysical mechanism. Biosensors use nucleic acids as receptors, coupled to a physicochemical signal transducer.

In various embodiments, biological sensors can use chromatographic or enzymatic immunoassay detection techniques. A detectable label allows for the detection of a ligand. A label can be chemically linked or conjugated to the ligand or synthetic RNA aptamer 10. The detectable label can be a fluorescent label, a radioactive label, an enzyme label, or a redox label.

In one embodiment, the biosensor is an apparatus to detect RDX 20. The apparatus is made of a housing configured to receive a sample and to retain synthetic RNA aptamer 10. Synthetic RNA aptamer 10 with a 3'-amino modification binds to a detectable label such as ferrocene. In this way, the presence of the detectable label in the housing shows RDX 20 is present in the sample.

It will be understood that many additional changes in the details, materials, procedures and arrangement of parts, which have been herein described and illustrated to explain the nature of the invention, may be made by those skilled in the art within the principle and scope of the invention as expressed in the appended claims. It should be understood that the drawings are not necessarily to scale; instead, emphasis has been placed upon illustrating the principles of the invention.

What is claimed is:

1. A composition of matter comprising: a synthetic RNA aptamer that binds 1,3,5-Trinitroperhydro-1,3,5-triazine (RDX), wherein said synthetic RNA aptamer consists of one or more optamers selected from the group consisting of: SEQ ID 1, 2, 3, 4, 5, 6, 7, 8, 9, 10, 12.

2. The composition of claim 1 wherein said synthetic RNA aptamer comprises the nucleotide sequence of SEQ ID. 1.

3. The composition of claim 1 wherein said synthetic RNA, aptamer comprises the nucleotide sequence of SEQ ID. 2.

4. The composition of claim 1 wherein said synthetic RNA aptamer comprises the nucleotide sequence of SEQ ID. 3.

5. The composition of claim 1 wherein said synthetic RNA aptamer comprises the nucleotide sequence of SEQ ID. 4.

6. The composition of claim 1 herein said synthetic RNA aptamer comprises the nucleotide sequence of SEQ ID. 5.

7. The composition of claim 1 wherein said synthetic RNA aptamer comprises the nucleotide sequence of SEQ ID. 6.

8. The composition of claim 1 wherein said synthetic RNA aptamer comprises the nucleotide sequence of SEQ ID. 7.

9. The composition of claim 1 wherein said synthetic RNA aptamer comprises the nucleotide sequence of SEQ ID. 8.

10. The composition of claim 1 wherein said synthetic RNA aptamer comprises the nucleotide sequence of SEQ ID. 9.

11. The composition of claim 1 wherein said synthetic RNA aptamer comprises the nucleotide sequence of SEQ ID. 10.

12. The composition of claim 1 wherein said synthetic RNA aptamer comprises the nucleotide sequence of SEQ ID. 11.

13. The composition of claim 1 wherein said synthetic RNA aptamer comprises the nucleotide sequence of SEQ ID. 12.

* * * * *